United States Patent
Urushiya (10) Patent No.: US 7,787,670 B2
(45) Date of Patent: Aug. 31, 2010

(54) RADIATION IMAGING DEVICE FOR CORRECTING BODY MOVEMENT, IMAGE PROCESSING METHOD, AND COMPUTER PROGRAM

(75) Inventor: Hiroyuki Urushiya, Saitama (JP)

(73) Assignee: Canon Kabushiki Kaisha, Tokyo (JP)

( * ) Notice: Subject to any disclaimer, the term of this patent is extended or adjusted under 35 U.S.C. 154(b) by 999 days.

(21) Appl. No.: 10/599,028

(22) PCT Filed: May 9, 2005

(86) PCT No.: PCT/JP2005/008817

§ 371 (c)(1),
(2), (4) Date: Sep. 18, 2006

(87) PCT Pub. No.: WO2005/107597

PCT Pub. Date: Nov. 17, 2005

(65) Prior Publication Data

US 2007/0195091 A1    Aug. 23, 2007

(30) Foreign Application Priority Data

May 11, 2004 (JP) .............................. 2004-141490

(51) Int. Cl.
*G06K 9/00* (2006.01)

(52) U.S. Cl. ........................ 382/128; 382/100; 382/130; 382/131; 382/132; 382/254; 382/276; 382/278; 378/11; 378/62; 378/63; 600/407; 600/410; 600/424; 600/425

(58) Field of Classification Search ................. 382/254, 382/275, 276, 278, 294; 378/11, 62, 63; 600/407, 410, 425, 424
See application file for complete search history.

(56) References Cited

U.S. PATENT DOCUMENTS 4,858,128 A * 8/1989 Nowak ....................... 382/131

(Continued)

FOREIGN PATENT DOCUMENTS

JP        6-114052        4/1994

(Continued)

OTHER PUBLICATIONS

Cooper et al. "Detection of Patient Motion During Tomographic Myocardial Perfusion Imaging", The Journal of Nuclear Medicine vol. 34 No. 8 1341-1348 1993).*

*Primary Examiner*—Andrew W Johns
*Assistant Examiner*—Jason Heidemann
(74) *Attorney, Agent, or Firm*—Fitzpatrick, Cella, Harper & Scinto (57) ABSTRACT

To perform as high-accuracy as possible a correction for a body movement for reducing an artifact occurring in a case of creating a tomographic image from an X-ray projected image, the coordinates of the respective corresponding points are acquired as between the projected images of which the projected angles overlap each other (e.g., 0° and 360° ), and a geometric transformation parameter is acquired through affine transformation or the like by using the set of the acquired coordinates. When an estimated amount of the acquired parameter is equal to or larger than a predetermined amount, the geometric transformation parameter for geometric correction is determined by using the acquired geometric transformation parameter, the geometric transformation (correction of body movement) is executed by using the determined geometric transformation parameter, and the tomographic image is created by using the corrected projected images.

13 Claims, 9 Drawing Sheets

U.S. PATENT DOCUMENTS

| | | | |
|---|---|---|---|
| 7,145,979 B2 | 12/2006 | Urushiya | 378/4 |
| 7,238,947 B2 | 7/2007 | Oumi et al. | 250/370.08 |
| 7,327,823 B2 * | 2/2008 | Matsuura | 378/8 |
| 2005/0276375 A1 | 12/2005 | Urushiya | 378/19 |
| 2006/0133564 A1 * | 6/2006 | Langan et al. | 378/8 |

FOREIGN PATENT DOCUMENTS

JP  2005-137472  6/2005

* cited by examiner

RADIATION IMAGING DEVICE FOR CORRECTING BODY MOVEMENT, IMAGE PROCESSING METHOD, AND COMPUTER PROGRAM

TECHNICAL FIELD

The present invention relates to a radiation imaging device, an image processing method for the radiation imaging device, and a computer program for causing the radiation imaging device to execute the image processing method. In particular, the radiation imaging device and the image processing method according to the present invention can be suitably used to reduce in radiography an artifact which occurs in a tomographic image due to movement of a body to be tested (this movement is called "body movement" hereinafter).

BACKGROUND ART

Figure 9:
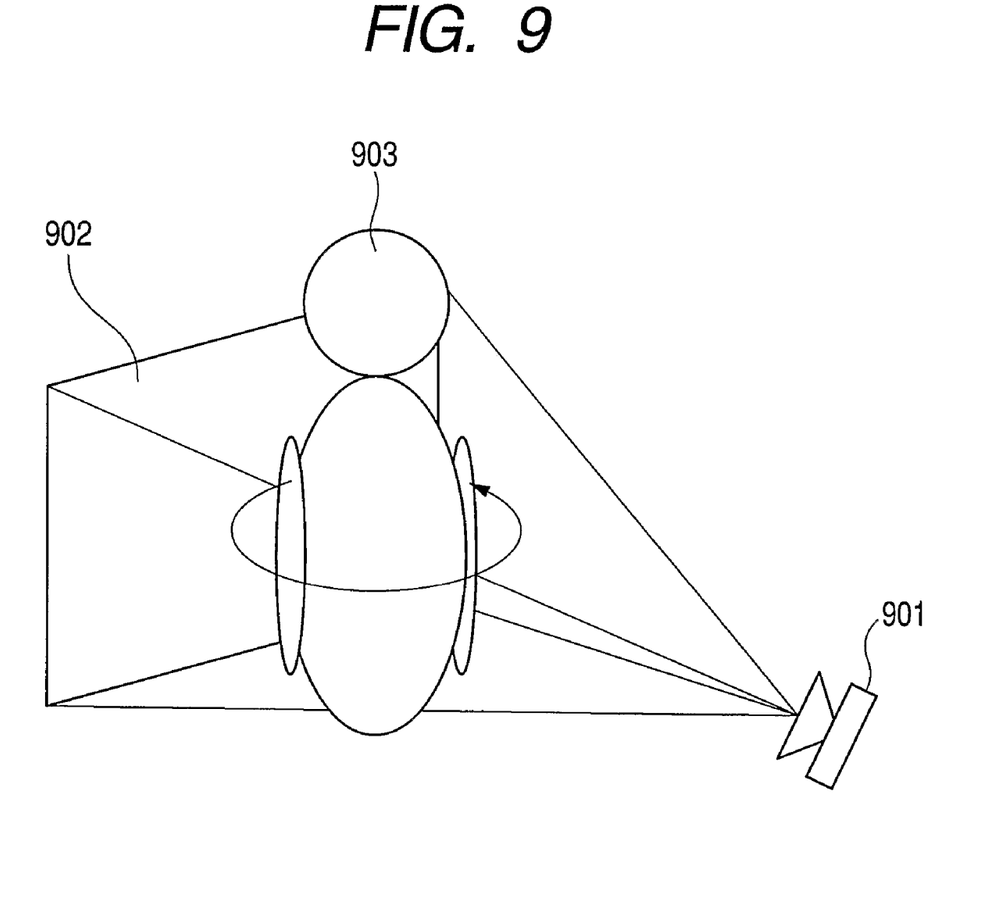
FIG. 9 is a conceptual diagram for explaining a conventional cone beam X-ray CT device.

FIG. 9 is a diagram showing a concept of a cone beam X-ray CT (computed tomography) device in which a plane sensor is used.

In FIG. 9, X-rays from an X-ray source 901 are transmitted through a body 903 to be tested, and the transmitted X-rays are detected by a plane sensor 902 provided at the position opposite to the X-ray source 901. Here, it should be noted that the body 903 to be tested is also called a "subject" 903 hereinafter. Then, while the system is generating the X-rays and detecting the radiated X-rays, the cone beam X-ray CT device executes control so that the X-ray source 901 and the plane sensor 902 together rotate around the subject 903. Alternately, it is possible to constitute the cone beam X-ray CT device so that the X-ray source 901 and the plane sensor 902 are fixed and instead the subject 903 itself rotates.

As above, when one rotation from 0° to 360° is executed, the X-ray source 901 and the plane sensor 902 each stand again in their respective initial positions. Alternately, when the subject 903 rotates from 0° to 360°, the subject 903 faces the initial direction at the initial position.

Incidentally, at that time, the projected image initially acquired by the plane sensor 902 at the angle 0° has to be the same as the projected image acquired after the rotation of 360°.

However, in actual radiography, there is no assurance that a patient who is the subject 903 does not move. That is, if the patient moves during the radiography, the projected image initially acquired by the plane sensor 902 at the angle 0° is consequently different from the projected image acquired after the rotation of 360°. Therefore, if the tomographic image of the subject 903 is created by using such different projected images, a streak artifact appears on the created tomographic image.

To reduce the artifact which appears due to such body movement, in conventional X-ray CT device in which the one-dimensional sensor is used, a method of correcting for deviation or misregistration of the subject occurring due to its body movement by executing interpolation within a range of certain angles is known (for example, see Japanese Patent Application Laid-Open No. H06-114052).

Figure 10A:
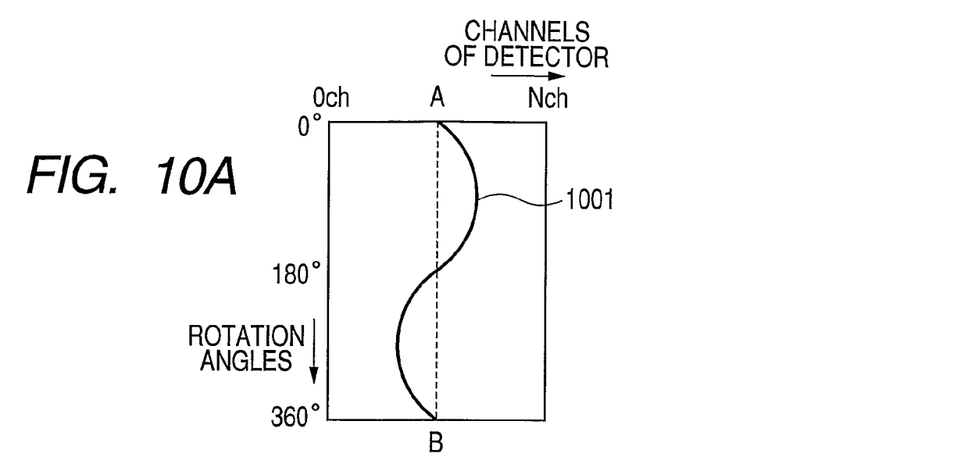
FIGS. 10A, 10B and 10C are conceptual diagrams for explaining conventional geometric transformation parameters for correcting for body movement.
Figure 10B:
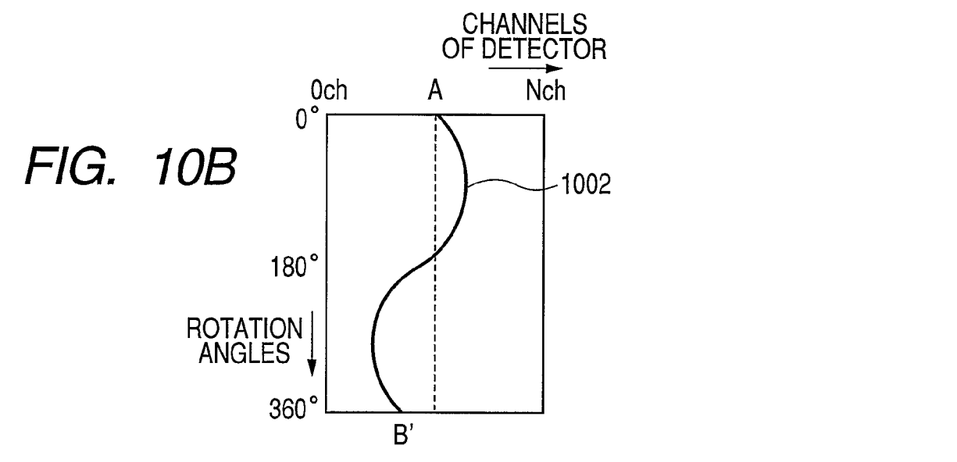
Figure 10C:
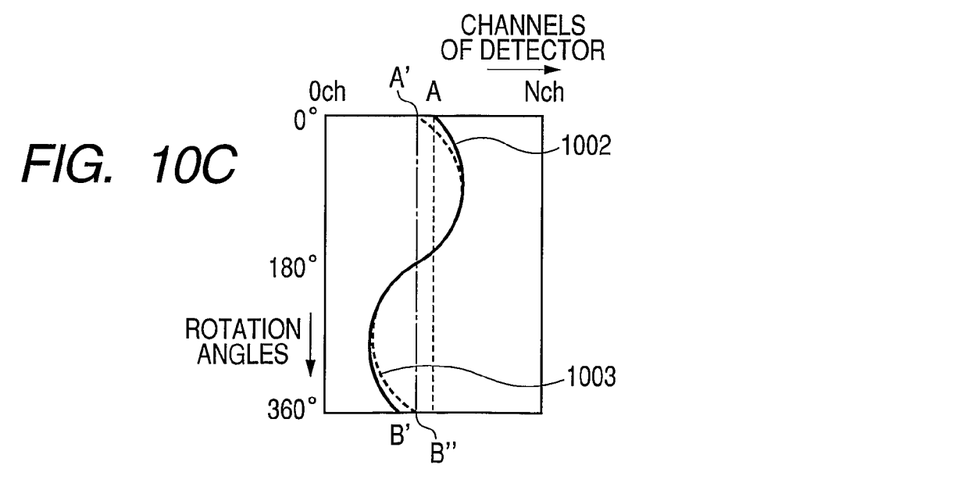

Subsequently, this method will be explained with reference to FIGS. 10A, 10B and 10C. Here, FIGS. 10A to 10C show a method in which the body movement is corrected by using a sinogram in which the channels of the detector are plotted on the axis of abscissa and rotation angles are plotted on the axis of ordinate. Here, it should be noted that each of the curved lines 1001 to 1003 on this sinogram indicates the trajectory of a certain point within the subject 903.

If the subject 903 does not move during the radiography (that is, there is no body movement of the subject 903), as shown in FIG. 10A, a detector channel position A of the point at the time of a start of scan (0°) conforms to a detector channel position B on the point at the time of an end of the scan (360°). On the other hand, if the body movement of the subject 903 occurs, as shown in FIG. 10B, the detector channel position of the point at the time of the end of the scan (360°) which should be essentially the position B shifts to a position B'.

To correct for such deviation or misregistration of the subject 903 occurring due to its body movement, as shown in FIG. 10C, the detector channel position A of the point at the time of the start of the scan (0°) is shifted to a position A' and the detector channel position B' on the point at the time of the end of the scan (360°) is likewise shifted to a position B" both by an amount half as much as a deviation amount between the detector channel position A of the point at the time of the start of scan (0°) and the detector channel position B' on the point at the time of the end of the scan (360°), so as to conform the position A' and the position B" to each other. Then, an interpolation process is executed on the data between the position A' and the position B" with respect to all the channels to acquire the data string indicated by the dotted curved line 1003 shown in FIG. 10C.

By using the above method, in conventional X-ray CT device in which the one-dimensional sensor is used, it is possible to reduce the artifact which appears due to the body movement of the subject 903. However, in the cone beam X-ray CT device in which the plane sensor 902 is used, if the above method is applied with respect to each of the horizontal lines constituting the plane sensor 902, there is a problem in that consistency between the adjacent horizontal lines cannot be sufficiently attained, and thus the body movement of the subject cannot be accurately corrected for.

Moreover, if it is judged by using the magnitude of deviation or misregistration of each horizontal line whether or not the body movement of the subject has occured, there is a problem that accurate judgment for the body movement cannot be attained, and consequently there is a concern that body movement may be needlessly corrected.

DISCLOSURE OF THE INVENTION

The present invention has been made in consideration of the above problems, and the object thereof is to perform a high-accuracy correction for body movement as much as possible, for reducing an artifact which appears on a tomographic image.

A radiation imaging device according to the present invention is characterized by comprising:

a geometric transformation parameter solving unit adapted to acquire, from among plural projected images of which projected angles of a radiation are different from others, geometric transformation parameters between at least the two projected images of which the projected angles of the radiation overlap each other;

a changing unit adapted to gradually change the geometric transformation parameters acquired by the geometric transformation parameter solving unit, within a predetermined range of the projected angles of the radiation; and a body movement correction unit adapted to execute a correction of a body movement by executing geometric transformation to the plural projected images of which the projected angles of the radiation are different, by using the respective changed geometric transformation parameters.

Moreover, an image processing method according to the present invention is characterized by comprising:

a geometric transformation parameter solving step of acquiring, from among plural projected images of which projected angles of a radiation are different from others, geometric transformation parameters between at least the two projected images of which the projected angles of the radiation overlap each other;

a changing step of gradually changing the geometric transformation parameters acquired in the geometric transformation parameter solving step, within a predetermined range of the projected angles of the radiation; and a body movement correction step of executing a correction of a body movement by executing geometric transformation to the plural projected images of which the projected angles of the radiation are different, by using the respective changed geometric transformation parameters.

BEST MODE FOR CARRYING OUT THE INVENTION

Hereinafter, the preferred embodiment of the present invention will be explained with reference to the attached drawings.

Figure 1:
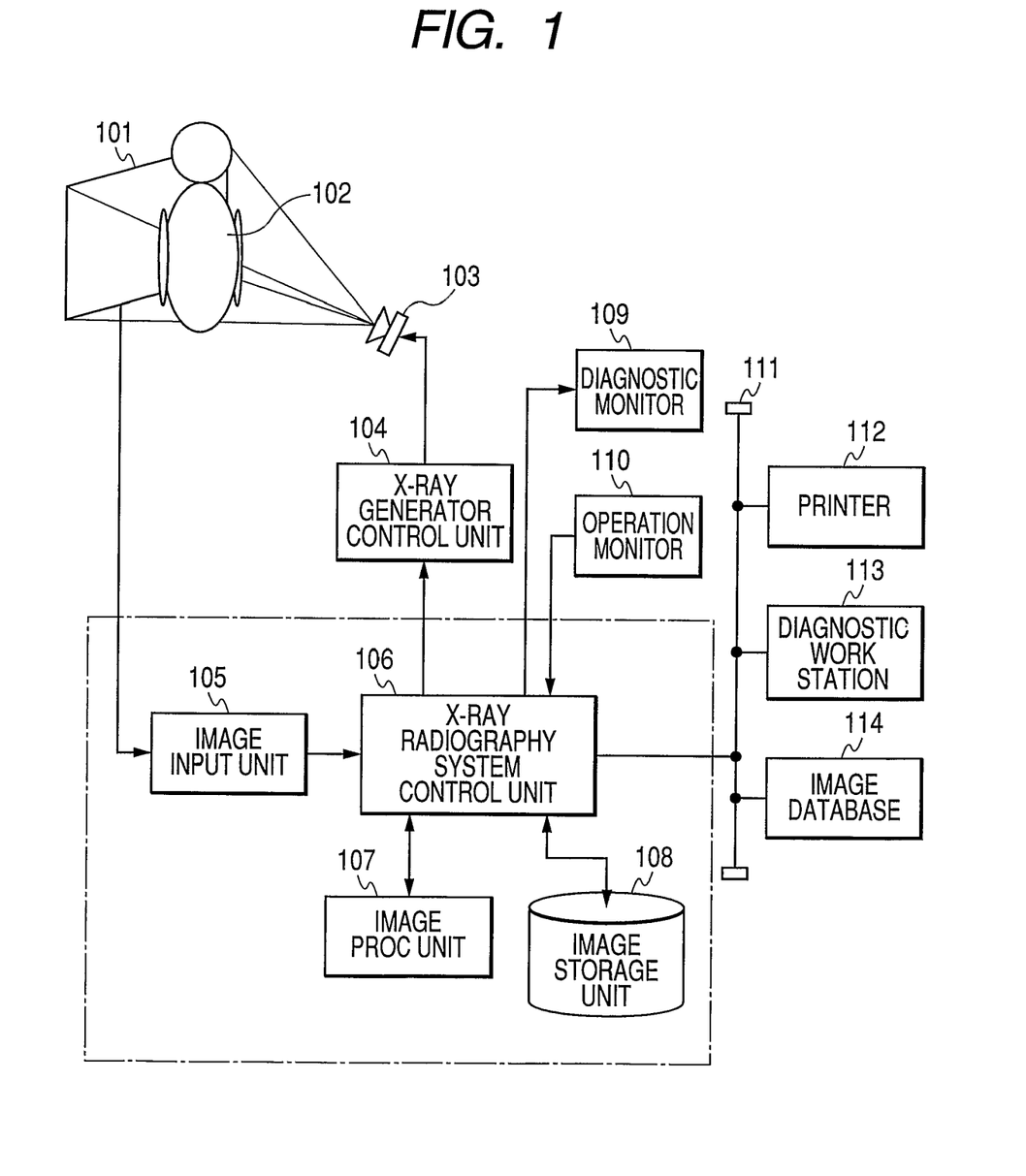
FIG. 1 is a block diagram showing one example of the whole constitution of an X-ray CT system according to the preferred embodiment of the present invention.

FIG. 1 is a block diagram showing one example of the whole constitution of an X-ray CT system according to the preferred embodiment of the present invention.

In FIG. 1, X-rays are generated from an X-ray source (or X-ray generator) 103 which is controlled by an X-ray generator control unit 104, the generated X-rays are transmitted through a patient 102 who is treated as a subject, and the transmitted X-rays are then detected by an X-ray detector 101. Incidentally, in the present embodiment, the case where X-rays are used will be explained by way of example. However, it is needless to say that the radiation to be processed in the present embodiment is not limited to the X-rays; that is, electromagnetic waves and such as $\alpha$-ray beams, $\beta$-ray beams, $\gamma$-rays and the like may be used.

The X-rays detected by the X-ray detector 101 are then input as a projected image to an image input unit 105. Incidentally, the X-ray source 103 and the X-ray detector 101 such as a plane sensor or the like collect the projected image with respect to each of predetermined rotation angles as together rotating around the patient 102. However, it is alternatively possible to rotate the patient 102, as the subject, who is fixed to a rotary table, as maintaining the positional relation of the patient 102 with respect to the X-ray source 103 and the X-ray detector 101.

Here, an image processing unit 107 corrects the X-ray detector 101, executes a pre-process including logarithmic transformation on the input projected image of each of the rotation angles, and further executes image processes such as a reconstruction process and the like on the input projected image. Thus, a group of tomographic images (also called a "tomographic image group") is created through the above processes. Then, the created tomographic image group can be displayed on a diagnostic monitor 109, and also stored in an image storage unit 108. In addition, it is possible to output the created tomographic image group to a printer 112, a diagnostic work station 113 or an image database 114 through a network 111.

Incidentally, a tester or a diagnostician handles an operation unit 110 to execute various operations such as a display window operation on the diagnostic monitor 109 or the like, a switching display operation of the tomographic image in the body axis of the patient 102, a cross section transformation operation of the tomographic image, a three-dimensional surface display operation, and the like. In the present embodiment, the above operations are totally managed by an X-ray radiography system control unit 106 which consists of a microcomputer and the like.

Figure 2:
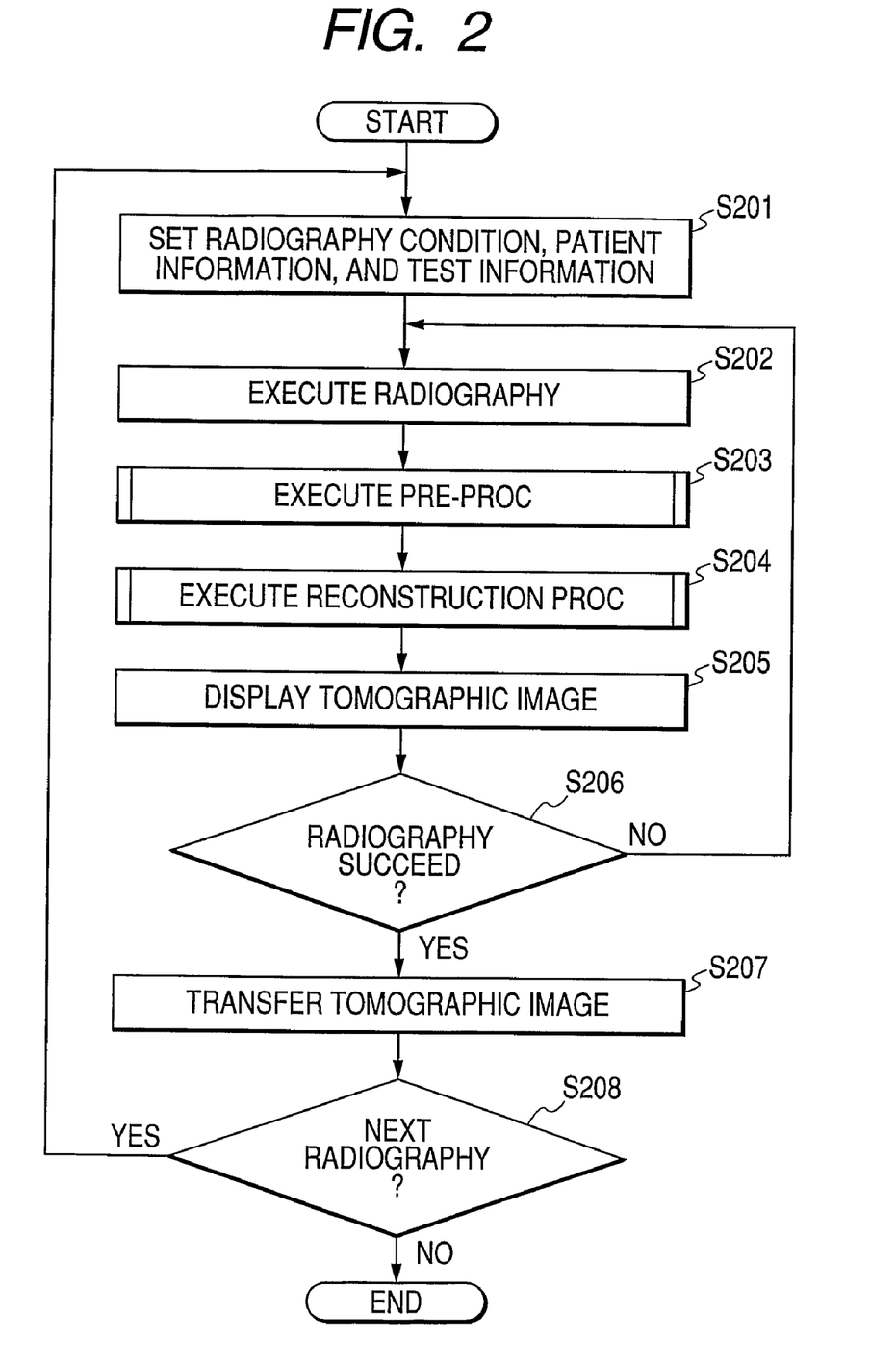
FIG. 2 is a flow chart for explaining one example of the operation to be executed by the X-ray CT system in case of radiographing a subject and thus acquiring a tomographic image, according to the embodiment of FIG. 1.

FIG. 2 is a flow chart for explaining one example of the operation to be executed by the X-ray CT system in case of radiographing the subject (CT radiography) and thus acquiring the tomographic image.

Initially, in step S201, radiography conditions such as an X-ray tube voltage, an X-ray tube current, an exposure time and the like, patient information such as the patient's name, age, gender and the like, and test information such as a test ID (identification) and the like are set through the operation by the tester on the operation unit 110.

Next, in step S202, the X-ray generator control unit 104 controls the X-ray source 103 in accordance with the radiography conditions set in step S201. Thus, the X-ray is generated from the X-ray source 103 to radiograph the patient 102, and the projected image acquired by the radiography is input to the image input unit 105.

Subsequently, in step S203, the image processing unit 107 executes the pre-process on the projected image acquired in the radiography. Then, in step S204, the image processing unit 107 further executes the reconstruction process to the projected image subjected to the pre-process in step S203. By doing so, the tomographic image of the patient 102 is created.

After then, in step S205, the tomographic image created in step S204 is displayed on the diagnostic monitor 109. Thus, the tester confirms the tomographic image displayed on the diagnostic monitor 109, and handles the operation unit 110 in accordance with the confirmed result. Subsequently, in step S206, the X-ray radiography system control unit 106 judges whether or not it is indicated that the X-ray radiography has succeeded, based on the content of the handling by the tester. Then, when the X-ray radiography system control unit 106 judges that it is indicated that the X-ray radiography has not succeeded, the flow returns to step S202 to repeat radiograph of the patient 102. That is, the processes in steps S202 to S206 are repeated until the X-ray radiography system control unit 106 judges that it is indicated that the X-ray radiography has succeeded. On the contrary, when the X-ray radiography system control unit 106 judges that it is indicated that the X-ray radiography succeeded, the flow advances to step S207. In step S207, the X-ray radiography system control unit 106 transfers the tomographic image created in step S205 to the image storage unit 108, the image database 114 and the like. Subsequently, in step S208, the X-ray radiography system control unit 106 judges whether or not next radiography is indicated, on the basis of the handling by the tester on the operation unit 110. Then, when the X-ray radiography system control unit 106 judges that the next radiography is indicated, the flow returns to step S201 to execute the next radiography. On the contrary, when the X-ray radiography system control unit 106 judges that the next radiography is not indicated, the operation to be executed by the X-ray CT system ends.

Figure 3:
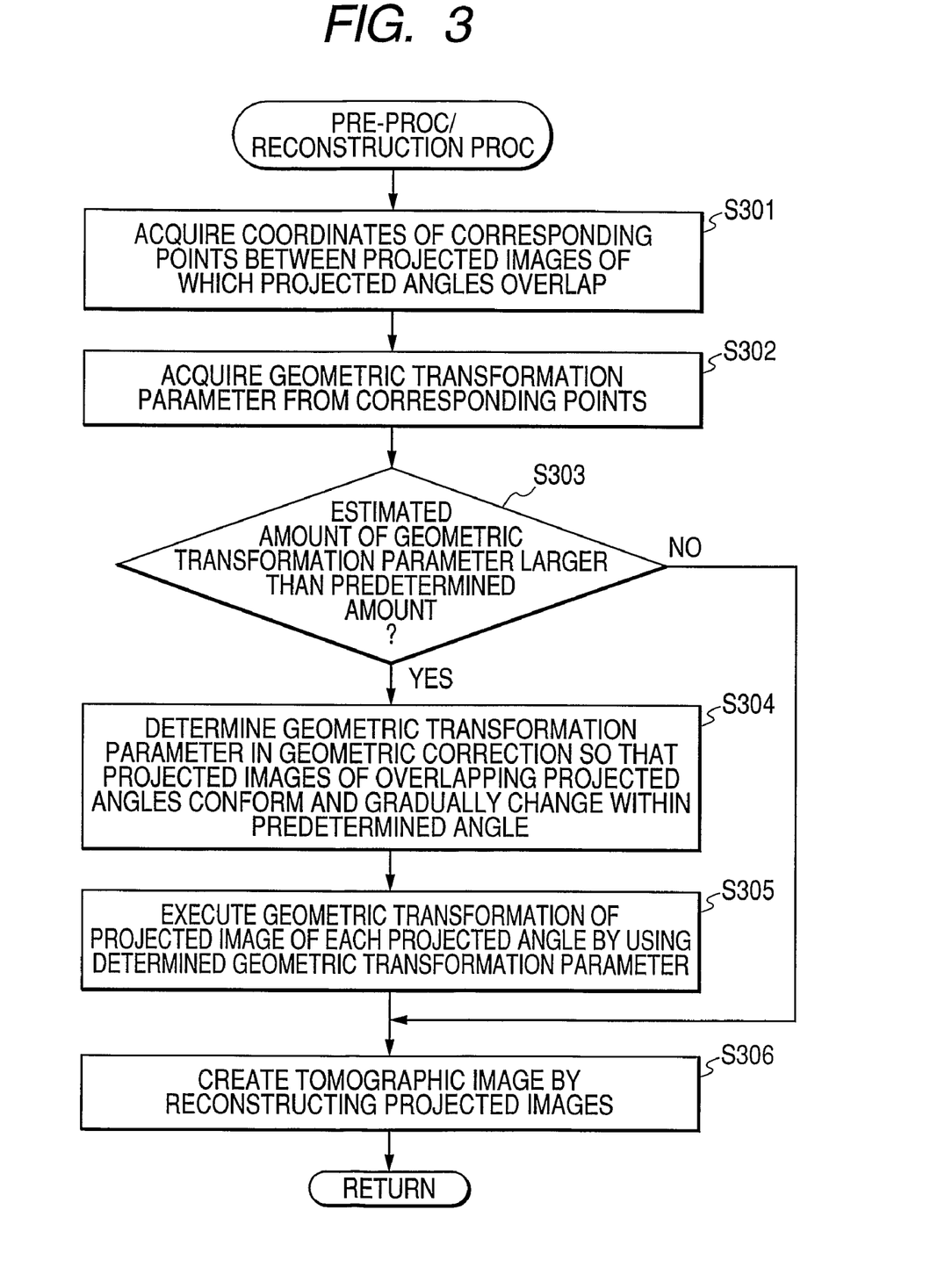
FIG. 3 is a flow chart for explaining one example of the operation to be executed in a pre-process and a reconstruction process of the X-ray CT system, according to the embodiment of FIG. 1.

FIG. 3 is a flow chart for explaining one example of the operation to be executed in the pre-process and the reconstruction process of the X-ray CT system, according to the present embodiment.

In FIG. 3, at the first place, the coordinates of the corresponding points between the two projected images of which the projected angles overlap each other are acquired (step S301). Here, in the following, a concrete example of the process to be executed in step S301 will be explained.

More specifically, for example, if the set of the X-ray source 103 and the X-ray detector 101 scans the patient 102 as just making a round (360°) of the patient 102, the projected angles which overlap each other may be set as 0° and 360° respectively. Also, if the set of the X-ray source 103 and the X-ray detector 101 executes the scan of 360° or more ((360+α)°), the projected angles which overlap each other may be set as θ° (<α) and (360+θ)°, respectively.

Figure 4:
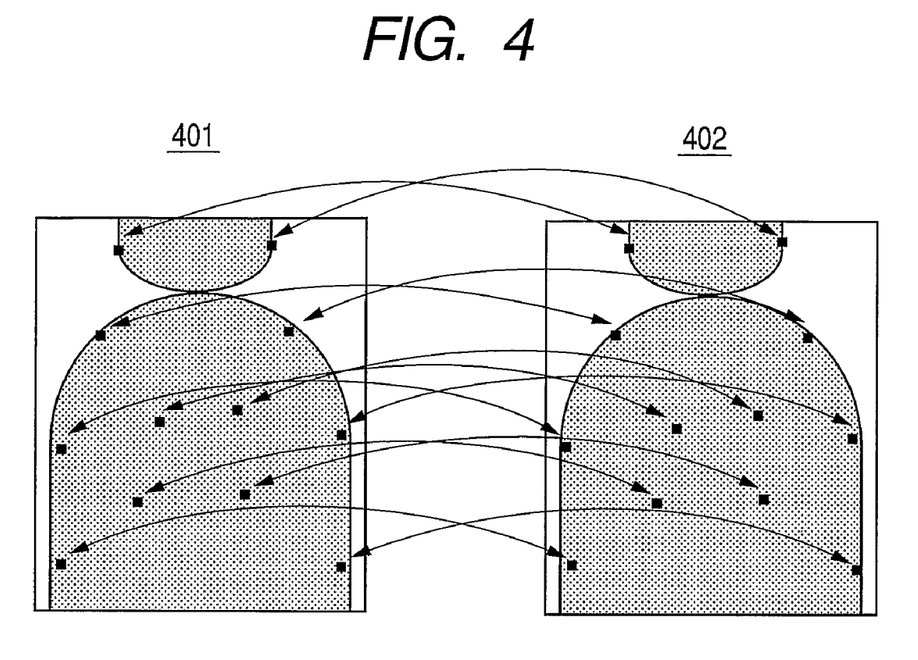
FIG. 4 is a conceptual diagram for explaining the corresponding points between two projected images of which the projected angles overlap each other, according to that embodiment.

FIG. 4 is a conceptual diagram for explaining the corresponding points between the two projected images of which the projected angles overlap each other. That is, as shown in FIG. 4, the coordinates of the corresponding points (the small black square points shown in FIG. 4) between a projected image 401 (for example, an image at scan angle 0°) and a projected image 402 (for example, an image at scan angle 360°) of which the respective projected angles overlap each other are acquired. Here, it should be noted that the number of corresponding points has to be equal to or larger than the number of geometric transformation parameters, and accuracy of the geometric transformation parameters improves in proportion to an increase in the number of corresponding points.

Figure 5:
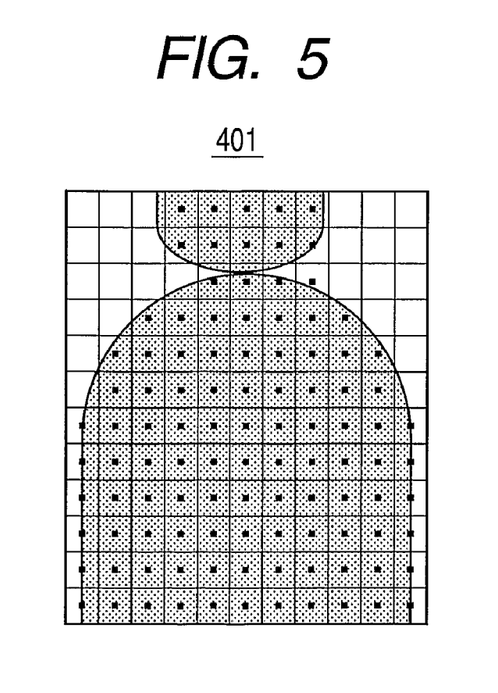
FIG. 5 is a conceptual diagram for explaining the fixed points on one of the two projected images of which the projected angles overlap each other, according to the foregoing embodiment.

However, if the number of corresponding points increases, the necessary calculation time becomes long as a result. Therefore, in consideration of such a fact, it has only to determine the number of corresponding points substantially in accordance with the system itself. In any case, the number of sets of the coordinates of the respective corresponding points of the projected images 401 and 402 that are acquired is equal to the number of corresponding points. To achieve this, first, plural fixed points are set on one (e.g., projected image 401) of the two projected images. Here, for example, it is preferable to use the most characteristic points as the fixed points. For example, with respect to the image of a chest, the end points of a rib, the branch points of lung blood vessels, and the like are suitable for the most characteristic points. Therefore, the end points of the rib, the branch points of the lung blood vessels or the like are set as the fixed points. In contrast, even if the characteristic points are not used as the fixed points, for example, as shown in FIG. 5, it has only to divide the entirety of the projected image 401 into numbers of small rectangles, and then set the respective central points of the divided small rectangles within the range of the subject as the fixed points.

Thus, if the plural fixed points are set with respect to one of the two projected images, the coordinates, on the other (e.g., projected image 402) of the two projected images, of the points respectively corresponding to these fixed points are acquired. To achieve this, it has only to use a matching method which is generally used in stereo analysis and the like. Hereinafter, an example of how to acquire the sets of the corresponding points by using the matching method will be explained with reference to FIGS. 6A and 6B.

Figure 6A:
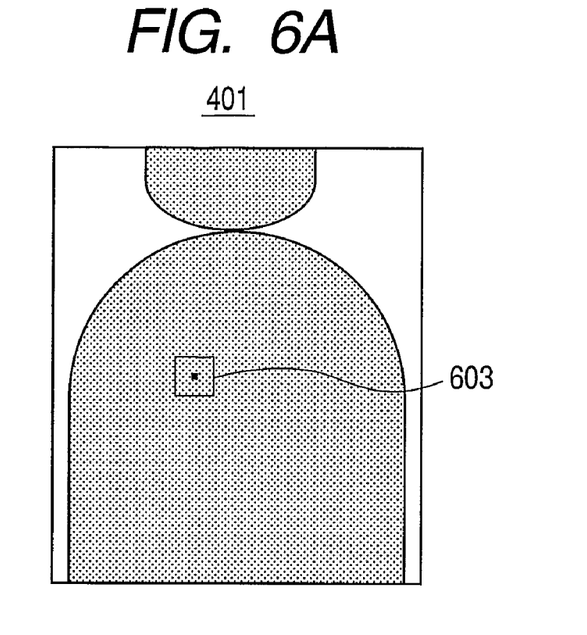
FIGS. 6A and 6B are conceptual diagrams for explaining how to acquire the corresponding points by means of matching, according to the foregoing embodiment.
Figure 6B:
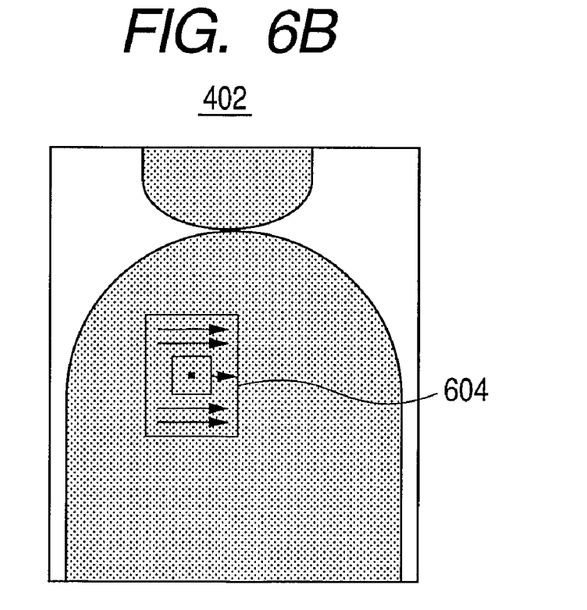

As shown in FIG. 6A, a template image 603 of a predetermined size is cut out on the basis of the fixed point on the projected image 401. Then, as shown in FIG. 6B, a search area 604 of a predetermined size larger than the size of the template image 603 is set on the projected image 402 of which the projected angle overlaps the projected angle of the projected image 401. Here, it should be noted that the coordinates of the central point of the search area 604 are the same as the coordinates of the fixed point on the projected image 401.

Then, the position of the central point is shifted sequentially from the upper left to the lower right within the search area 604. At the same time, a reference image of the size same as that of the template image 603 is cut out from the projected image 402. Subsequently, an estimated value est concerning the matching between the cut-out reference image and the template image 603 is acquired.

Here, if it is assumed that the coordinates of the reference image are given as r(x, y) and the coordinates of the template image 603 are given as t(x, y), the estimated value est of the matching can be acquired by the following equation (1):

$$est = \frac{\sum_{k=1}^{n}\sum_{l=1}^{m}\{r(k,l)-\bar{r}\}\cdot\{t(k,l)-\bar{t}\}}{\sqrt{\sum_{k=1}^{n}\sum_{l=1}^{m}\{r(k,l)-\bar{r}\}^2}\cdot\sqrt{\sum_{k=1}^{n}\sum_{l=1}^{m}\{t(k,l)-\bar{t}\}^2}} \quad (1)$$

Here, it should be noted that, in the above equation (1), the symbols n and m respectively denote pixel sizes of the template image 603, and the horizontal lines (−) added above the characters r and t indicate the average values of those respective variables.

Incidentally, when it is requested to execute the calculation at high speed, the estimated value est of the matching may be acquired simply by the following equation (2):

$$est = \sum_{k=1}^{n}\sum_{l=1}^{m}|r(k,l)-t(k,l)| \quad (2)$$

That is, the position of the reference image at which the estimated value est of the matching becomes minimum is equivalent to the coordinates of the corresponding points.

In any case, when the coordinates of the corresponding points between the projected images 401 and 402 of which the projected angles overlap each other are acquired in step S301, the geometric transformation parameter is acquired from the set of the coordinates of the corresponding points (step S302). For example, an affine transformation may be used in such geometric transformation.

It should be noted that the affine transformation can be represented by the following equation (3):

$$\begin{pmatrix} x' \\ y' \end{pmatrix} = \begin{pmatrix} a_{11} & a_{12} \\ a_{21} & a_{22} \end{pmatrix} \begin{pmatrix} x \\ y \end{pmatrix} + \begin{pmatrix} a_{01} \\ a_{02} \end{pmatrix} \quad (3)$$

Then, the set of the corresponding points is defined as the set of the point of the coordinates $(x_n, y_n)$ and the point of the coordinates $(X_n, Y_n)$ (n is 1, ..., N). Subsequently, geometric transformation parameters $a_{01}, a_{02}, a_{11}, a_{12}, a_{21}, a_{22}$ for the affine transformation by which a least squares error err between the coordinates $(x_n', y_n')$ acquired by transforming the coordinates $(x_n, y_n)$ with use of the above equation (3) and the coordinates $(X_n, Y_n)$ is minimized are acquired. Incidentally, the least squares error err is represented by the following equation (4):

$$err = \sum_{n=1}^{N} \sqrt{(X_n - x_n')^2 + (Y_n - y_n')^2} \quad (4)$$

Here, the coordinates $x_n'$ and $y_n'$ are the functions which use the geometric transformation parameters $a_{01}, a_{02}, a_{11}, a_{12}, a_{21}, a_{22}$ for the affine transformation as variables. Therefore, also the least squares error err by the equation (4) is the function which uses the geometric transformation parameters $a_{01}, a_{02}, a_{11}, a_{12}, a_{21}, a_{22}$ for the affine transformation as variables.

For this reason, if the least squares error err is subjected to partial differentiation based on each of the variables of the geometric transformation parameters $a_{01}, a_{02}, a_{11}, a_{12}, a_{21}, a_{22}$ for the affine transformation to set "0" and then the simultaneous equations are solved, it is possible to acquire the geometric transformation parameters $a_{01}, a_{02}, a_{11}, a_{12}, a_{21}, a_{22}$ for the affine transformation by which the least squares error err becomes minimum.

In this way, when the affine transformation is executed, the geometric transformation parameters $a_{01}, a_{02}, a_{11}, a_{12}, a_{21}, a_{22}$ for the affine transformation are acquired. However, when the affine transformation is executed, the geometric transformation in which also enlargement of the image and shearing of the image are admitted. Consequently, in case of executing the geometric transformation only for rotation of the image and movement of the image without permitting enlargement and shearing of the image, Helmert transformation is used. Here, it should be noted that the Helmert transformation can be represented by the following equation (5):

$$\begin{pmatrix} x' \\ y' \end{pmatrix} = \begin{pmatrix} \cos\theta & \sin\theta \\ -\sin\theta & \cos\theta \end{pmatrix} \begin{pmatrix} x \\ y \end{pmatrix} + \begin{pmatrix} a_{01} \\ a_{02} \end{pmatrix} \quad (5)$$

That is, the geometric transformation parameters in case of the Helmert transformation are three, i.e., $\theta, a_{01}, a_{02}$. Therefore, these parameters can be acquired in the same manner as above.

In addition to the affine transformation and the Helmert transformation, even if a secondary projective transformation, high-order polynomial transformation or the like is used, it is possible to acquire the geometric transformation parameters as well as the case where the affine transformation, the Helmert transformation or the like is used.

In any case, when the geometric transformation parameter is acquired in step S302, it is then judged whether or not an estimated amount of the acquired geometric transformation parameter is larger than a predetermined amount (step S303).

Here, it should be noted that the estimated amount of the geometric transformation parameter is the amount for estimating the magnitude of the body movement while the scan is being executed. More specifically, the estimated amount of the geometric transformation parameter is used to estimate how far from the geometric transformation parameter in case of no body movement.

Incidentally, for example, it is assumed that the geometric transformation parameters are set as $\lambda_1, \lambda_2, \ldots, \lambda_n, \ldots, \lambda_N$, and the geometric transformation parameters in a case of no body movement are set as $\lambda_1', \lambda_2', \ldots \lambda_n', \ldots, \lambda_N'$. On such a premise, an estimated amount est2 of the geometric transformation parameter can be acquired by the following equation (6):

$$est2 = \sqrt{\sum_{n=1}^{N} (\lambda_n' - \lambda_n)^2} \quad (6)$$

Here, it should be noted that the right side of the above equation (6) may not be necessarily the square root. That is, instead of the above equation (6), it is possible to more simply acquire the estimated amount est2 of the geometric transformation parameter by the following equation (7):

$$est2 = \sum_{n=1}^{N} |\lambda_n' - \lambda_n| \quad (7)$$

By the way, if the affine transformation is adopted as the geometric transformation, the following equations (8) are satisfied:

$$\lambda_1 = a\lambda_{01}, \lambda_2 = a\lambda_{02}, \lambda_3 = a\lambda_{11}, \lambda_4 = a_{12}, \lambda_5 = a_{21}, \lambda_6 = a_{22}$$

$$\lambda_1' = 0, \lambda_2' = 0, \lambda_3' = 1, \lambda_4' = 0, \lambda_5' = 0, \lambda_6' = 1 \quad (8)$$

Moreover, if the Helmert transformation is adopted as the geometric transformation, the following equations (9) are satisfied:

$$\lambda_1 = \theta, \lambda_2 = a\lambda_{01}, \lambda_3 = a\lambda_{01}$$

$$\lambda_1' = 0, \lambda_2' = 0, \lambda_3' = 0 \quad (9)$$

In any case, when it is judged in step S303 that the estimated amount of the geometric transformation parameter acquired as above is equal to or smaller than a predetermined amount, it is possible to judge that there is no body movement of the level for which the correction is necessary. Therefore, in this case, the flow advances to step S306 without executing the correction for the body movement so as to reconstruct the projected image and thus create the tomographic image.

On the other hand, when it is judged in step S303 that the estimated amount of the geometric transformation parameter acquired as above is larger than the predetermined amount, the correction for the body movement is executed.

More specifically, to execute the correction for the body movement, the geometric transformation parameter for geometric correction is first determined so that the projected images of which the projected angles overlap each other conform to each other and gradually change within a predetermined angle (step S304).

In the correction for the body movement, only half of the correction amount is gradually subjected to the correction according to the angles within the range, e.g., from 0° to 180°. Subsequently, within the range from 180° to 360°, the correction is gradually executed according to the angles in the direction opposite to the direction of the correction within the rage from 0° to 180°, whereby it is possible to achieve the smooth correction of the body movement.

With respect to the geometric transformation parameters for executing the above correction of the body movement (geometric correction), only half of the geometric transformation parameters acquired in step S302 may be determined so as to gradually change within the range, e.g., from 0° to 180°. Besides, only half of the minus geometric transformation parameters acquired in step S302 may be determined so as to gradually change within the range, e.g., from 180° to 360°.

In addition, the body movement is gradually corrected according to the angles within the range from 0° to 90°, by half of the correction amount of the body movement. Within the range from 90° to 270°, the body movement is not corrected for. Then, within the range from 270° to 360°, the body movement is gradually corrected for according to the angles, by half of the correction amount of the body movement, in the direction opposite to the direction of the correction within the rage from 0° to 90°.

More specifically, the meaning that the projected image gradually changes within the predetermined angle and the body movement is gradually corrected for according to the angles is as follows. That is, the geometric transformation parameter is divided by the predetermined angle to acquire a change amount of the geometric transformation parameter with respect to each unit angle, and the change amounts of the geometric transformation parameters of the respective unit angles are gradually added to others.

Here, one example of the method of determining the geometric transformation parameters for executing the correction of the body movement (geometric correction) will be explained with reference to FIG. 7.

Figure 7:
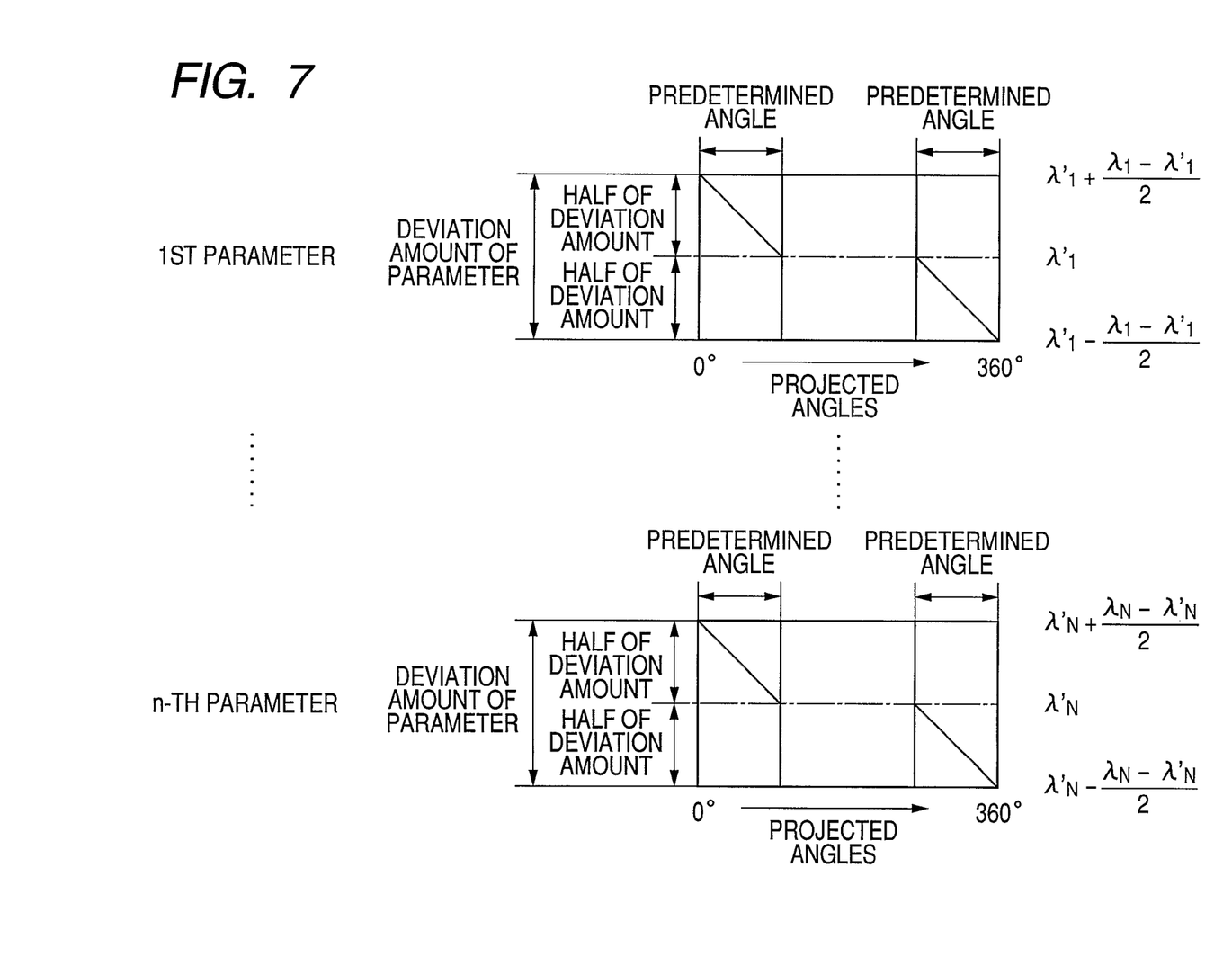
FIG. 7 is a conceptual diagram for explaining geometric transformation parameters for correcting body movement, according to the foregoing embodiment of the present invention.

That is, FIG. 7 shows the projected angles in the direction along the axis of abscissas and the geometric transformation parameters in the direction along the axis of ordinate, with respect to each of the respective geometric transformation parameters. In FIG. 7, the angles from 0° to 360° are given as the projected angles. However, when the scan of an angle exceeding 360° ((360+'α)°) is executed, the projected angle may be set from θ° (<α) to (360+θ)°.

Here, it takes the case of n-th parameter as an example. The geometric transformation is executed by half of the body movement with respect to the projected image of 0°, and so its parameter $\mu_n(0)$ is given by the following equation (10):

$$\mu_n(0) = \lambda_n' + (\lambda_n - \lambda_n')/2 \quad (10)$$

Then, for example, it is assumed that the above predetermined angle is ω°. In such a case, since the geometric transformation is not executed within the range from ω° to (360−ω°)°, the parameter of the projected angle within this range is assumed as $\lambda_n'$ for the sake of convenience. Here, within the range from 0° to ω°, it is controlled to gradually change the parameter from $\mu_n(0)$ to $\lambda_n'$. That is, the parameter $\mu_n(\beta)$ in case of β° (<ω) is given by the following equation (11):

$$v_n(\beta) = \lambda_n' + \{(\lambda_n - \lambda_n')/2\} \times \beta/\omega \quad (11)$$

Similarly, the geometric transformation is executed by half of the body movement with respect to the projected image of 360°, and so its parameter $\mu_n(360)$ is given by the following equation (12):

$$\mu_n(360) = \lambda_n' - (\lambda_n - \lambda_n')/2 \quad (12)$$

Then, within the range from (360−ω)° to 360°, it is controlled to gradually change the parameter from $\lambda_n'$ to $\mu_n(360)$. That is, the parameter $\mu_n(\gamma)$ of the range from (360−ω)° to 360° is given by the following equation (13):

$$\mu_n(\gamma) = \lambda_n' + \{(\lambda_n - \lambda_n')/2\} \times \{\gamma - (360-\omega)\}/\omega \quad (13)$$

These parameters are respectively used to execute the geometric correction by half with respect to the side of 0° and also to execute the geometric correction by half with respect to the side of 360°. However, the parameter may be determined so that the whole transformation is executed within the predetermined angle with respect to either the side of 0° or the side of 360°.

Then, when the geometric transformation parameters for correcting for the body movement are acquired, the geometric transformation is executed on the projected image of each of the projected angles by using the acquired geometric transformation parameter (step S305). However, it should be noted that the geometric transformation is not executed within the range from ω° to (360−ω)°.

Figure 8:
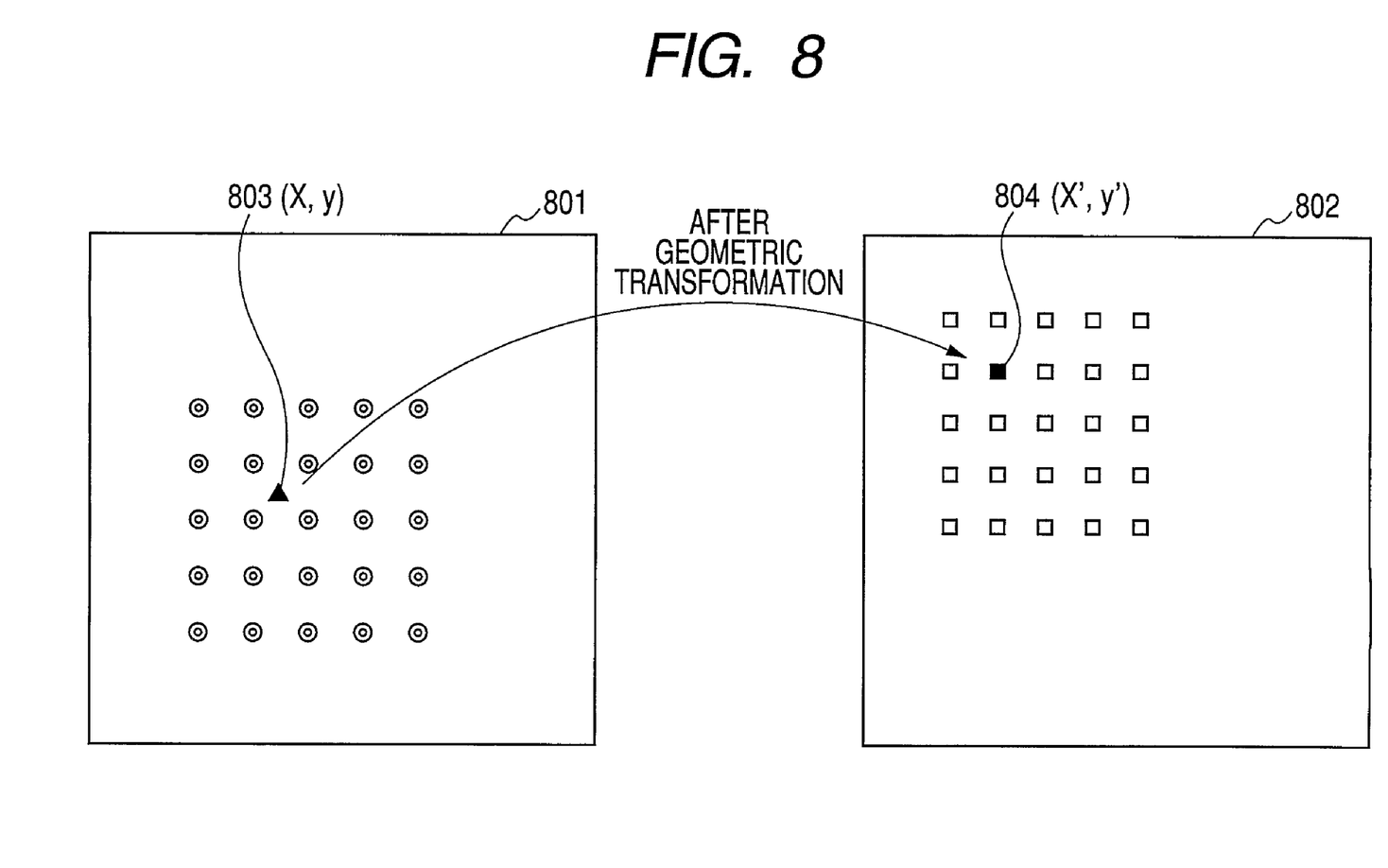
FIG. 8 is a conceptual diagram for explaining the coordinates which show the status before the geometric transformation is executed and the coordinates which show the status after the geometric transformation has been executed.

Now, one example of the geometric transformation will be explained with reference to FIG. 8. In FIG. 8, it is assumed that, through the geometric transformation, a point (X, y) indicated by numeral 803 on a projected image 801 which is acquired before the geometric transformation is executed (hereinafter, called a "before-geometric transformation image" 801) is transformed into a point (X', y') indicated by numeral 804 on a projected image 802 which is acquired after the geometric transformation is executed (hereinafter, called an "after-geometric transformation image" 802).

When an image is created through the geometric transformation, the process opposite to the above is used. That is, the point (X, y) on the before-geometric transformation image 801 to be transformed into the point (X', y') on the after-geometric transformation image 802 is acquired. Here, it should be noted that the point (X', y') indicates the coordinates of the integer value corresponding to each pixel on the after-geometric transformation image 802. Then, by using the inverse transformation of the geometric transformation with respect to the coordinates, the point (X, y) corresponding to the point (X', y') can be acquired. However, since the point (X, y) does not have the coordinates of an integer value, interpolation is executed by using the pixel values of the four points closest to the point (X, y), and the interpolated value is set as the pixel value of the point (X', y'). This process is executed on all the pixels, whereby the image can be created through the geometric transformation.

Incidentally, when the image is created through the geometric transformation as above, the geometric transformation is not directly used, but the inverse transformation of the geometric transformation is used. For this reason, the geometric transformation parameter may be set in advance as the parameter for the inverse transformation of the geometric transformation in step S304.

In any case, when the correction for the body movement through the geometric transformation ends, the reconstruction is executed by using the corrected projected images, and the tomographic image is thus created (step S306).

As described above, in the present embodiment, the coordinates of the respective corresponding points between the projected images 401 and 402 of which the respective projected angles (for example, 0° and 360°) overlap each other are first acquired. Then, the geometric transformation parameters $\mu_n(0)$ and $\mu_n(360)$ are acquired through the affine transformation or the like by using the sets of the coordinates of the corresponding points. Subsequently, when the estimated amount of the geometric transformation parameter is larger than the predetermined amount, the correction for the body movement is executed, and the tomographic image is then created by using the projected image 802 which has been subjected to the correction for the body movement.

More specifically, when the correction for the body movement is executed, as described above, the geometric transformation parameter for executing the geometric correction with respect to the projected angles from $\omega°$ to $(360-\omega)°$ is assumed as $\lambda_n'$ for the sake of convenience. Then, the geometric transformation parameter $\mu_n(\beta)$ for executing the geometric correction is determined so that the parameter gradually changes from $\mu_n(0)$ to $\lambda_n'$ (as indicated by the equation (11)) within the range of the projected angles from 0° to $\omega°$. Moreover, the geometric transformation parameter $\mu_n(\gamma)$ for executing the geometric correction is determined so that the parameter gradually changes from $\lambda_n'$ to $\mu_n(360)$ (as indicated by the equation (13)) within the range of the projected angles from $(360-\omega)°$ to 360°. After then, the geometric transformation (i.e., body movement correction) is executed on the projected images having the projected angles from 0° to $\omega°$ and on the projected images having the projected angles from $(360-\omega)°$ to 360°.

As described above, according to the present embodiment, the body movement (that is, the movement of the subject) is not dealt with respect to each horizontal (landscape) line, but as the image. Thus, the body movement can be accurately identified and measured, whereby it is possible to achieve high-precision correction for the body movement, and it is also possible to achieve smooth correction for the body movement. In consequence, it is possible to create a tomographic image on which an artifact has been reduced by correcting for the body movement.

Other Embodiments of the Present Invention

Incidentally, the present invention includes in its category a case where program codes of software for realizing the functions of the above embodiment are supplied to a computer provided in an apparatus or a system connected to various devices so as to actually operate these devices for realizing the functions of the above embodiment, and thus the computer (CPU or MPU) in the system or the apparatus reads and executes the supplied and stored program codes and operates these devices.

In this case, the program codes themselves of the software realize the functions of the above embodiment. Therefore, the program codes themselves, and a means such as a recording medium storing these program codes, for supplying the program codes to the computer constitute the present invention. As the recording medium for storing these program codes, for example, a flexible disk, a hard disk, an optical disk, a magnetooptical disk, a. CD-ROM, a magnetic tape, a nonvolatile memory card, a ROM or the like can be used.

Moreover, it is needless to say that the present invention includes not only a case where the functions of the above embodiment are realized by executing the supplied program codes using a computer, but also a case where the program codes cooperate with an OS (operating system) running on the computer or other application software to realize the functions of the above embodiment.

Furthermore, it is needless to say that the present invention also includes a case where, after the supplied program codes are written into a function expansion board inserted in the computer or a memory of a function expansion unit connected to the computer, the CPU or the like provided in the function expansion board or the function expansion unit executes a part or all of the actual processes on the basis of the instructions of the program codes, and thus the functions of the above embodiment are realized by such the processes.

According to the present embodiment, body movement of the subject can be determined from the image. Thus, the body movement can be accurately identified and measured. In addition, the geometric transformation parameters are smoothly changed between the projected angles, whereby it is possible to achieve high-precision correction for the body movement as much as possible. In consequence, it is possible to create a tomographic image on which an artifact has been reduced as much as possible.

According to another aspect of the present invention, the magnitude of the body movement is estimated by using the acquired geometric transformation parameters, and the correction for the body movement is executed only in the case where the magnitude of the body movement is equal to or larger than the predetermined magnitude. Thus, useless correction of the body movement can be avoided, whereby it is possible to shorten the time necessary for executing the correction for the body movement.

This application claims priority from Japanese Patent Application No. 2004-141490 filed May 11, 2004, which is hereby incorporated by reference herein.

The invention claimed is:

1. A radiation imaging device comprising:
a geometric transformation parameter solving unit adapted to acquire, from among plural projected images of which projected angles of a radiation are different from others, geometric transformation parameters between at least the two projected images of which the projected angles of the radiation overlap each other;
a changing unit adapted to gradually change the geometric transformation parameters acquired by said geometric transformation parameter solving unit, within a predetermined range of the projected angles of the radiation; and
a body movement correction unit adapted to execute a correction of a body movement by executing geometric transformation to the plural projected images of which the projected angles of the radiation are different, by using the respective geometric transformation parameters changed by said changing unit.

2. A radiation imaging device according to claim 1, further comprising an estimation unit adapted to estimate magnitude of the body movement by using the geometric transformation parameter acquired by said geometric transformation parameter solving unit,
wherein said body movement correction unit executes the correction of the body movement in a case where it is judged by said estimation unit that the magnitude of the body movement is equal to or larger than predetermined magnitude.

3. A radiation imaging device according to claim 2, further comprising a tomographic image creation unit adapted to create, in the case where it is judged by said estimation unit that the magnitude of the body movement is equal to or larger than the predetermined magnitude, a tomographic image by reconstructing the projected images of which the correction of the body movement has been executed by said body movement correction unit, and create, in a case where it is judged by said estimation unit that the magnitude of the body movement is smaller than the predetermined magnitude, the tomographic image by using the projected images of which the correction of the body movement is not executed by said body movement correction unit.

4. A radiation imaging device according to claim 1, wherein said geometric transformation parameter solving unit acquires coordinates of corresponding points on at least the two projected images of which the projected angles of the radiation overlap each other, and acquires, by using the acquired coordinates of the corresponding points, the geometric transformation parameters between at least the two projected images of which the projected angles of the radiation overlap each other, and said body movement correction unit gradually changes, within the predetermined range of the projected angles of the radiation, the geometric transformation parameters acquired by said geometric transformation parameter solving unit, determines the changed geometric transformation parameters as geometric transformation parameters of geometric correction, and executes the geometric transformation to the projected images of which the projected angles of the radiation are within the predetermined range by using the determined geometric transformation parameters of the geometric correction.

5. A radiation imaging device according to claim 4, wherein said geometric transformation parameter solving unit acquires the coordinates of the corresponding points on at least the two projected images of which the projected angles of the radiation overlap each other, by using a matching method.

6. A radiation imaging device according to claim 1, wherein said geometric transformation parameter solving unit acquires the geometric transformation parameters between at least the two projected images of which the projected angles of the radiation overlap each other, by using any one of affine transformation, Helmert transformation, secondary projective transformation and high-order polynomial transformation.

7. An image processing method comprising:

a geometric transformation parameter solving step of acquiring, from among plural projected images of which projected angles of a radiation are different from others, geometric transformation parameters between at least the two projected images of which the projected angles of the radiation overlap each other;

a changing step of gradually changing the geometric transformation parameters acquired in said geometric transformation parameter solving step, within a predetermined range of the projected angles of the radiation; and a body movement correction step of executing a correction of a body movement by executing geometric transformation to the plural projected images of which the projected angles of the radiation are different, by using the respective changed geometric transformation parameters.

8. An image processing method according to claim 7, further comprising an estimation step of estimating magnitude of the body movement by using the geometric transformation parameter acquired in said geometric transformation parameter solving step, wherein said body movement correction step is adapted to execute the correction of the body movement in a case where it is judged in said estimation step that the magnitude of the body movement is equal to or larger than predetermined magnitude.

9. An image processing method according to claim 8, further comprising a tomographic image creation step of creating, in the case where it is judged in said estimation step that the magnitude of the body movement is equal to or larger than the predetermined magnitude, a tomographic image by reconstructing the projected images of which the correction of the body movement has been executed in said body movement correction step, and creating, in a case where it is judged in said estimation step that the magnitude of the body movement is smaller than the predetermined magnitude, the tomographic image by using the projected images of which the correction of the body movement is not executed in said body movement correction step.

10. An image processing method according to claim 7, wherein said geometric transformation parameter solving step is adapted to acquire coordinates of corresponding points on at least the two projected images of which the projected angles of the radiation overlap each other, and acquire, by using the acquired coordinates of the corresponding points, the geometric transformation parameters between at least the two projected images of which the projected angles of the radiation overlap each other, and said body movement correction step is adapted to gradually change, within the predetermined range of the projected angles of the radiation, the geometric transformation parameters acquired in said geometric transformation parameter solving step, determine the changed geometric transformation parameters as geometric transformation parameters of geometric correction, and execute the geometric transformation to the projected images of which the projected angles of the radiation are within the predetermined range by using the determined geometric transformation parameters of the geometric correction.

11. An image processing method according to claim 10, wherein said geometric transformation parameter solving step is adapted to acquire the coordinates of the corresponding points on at least the two projected images of which the projected angles of the radiation overlap each other, by using a matching method.

12. An image processing method according to claim 7, wherein said geometric transformation parameter solving step is adapted to acquire the geometric transformation parameters between at least the two projected images of which the projected angles of the radiation overlap each other, by using any one of affine transformation, Helmert transformation, secondary projective transformation and high-order polynomial transformation.

13. A computer-readable medium containing a computer program for causing a computer to execute:

a geometric transformation parameter solving step of acquiring, from among plural projected images of which projected angles of a radiation are different from others, geometric transformation parameters between at least the two projected images of which the projected angles of the radiation overlap each other;

a changing step of gradually changing the geometric transformation parameters acquired in said geometric transformation parameter solving step, within a predetermined range of the projected angles of the radiation; and a body movement correction step of executing a correction of a body movement by executing geometric transformation to the plural projected images of which the projected angles of the radiation are different, by using the respective changed geometric transformation parameters.

* * * * *